United States Patent [19]

Fujimori et al.

[11] Patent Number: 5,446,027
[45] Date of Patent: Aug. 29, 1995

[54] AMIDE DERIVATIVE AND EXTERNAL SKIN CARE PREPARATION CONTAINING THE SAME

[75] Inventors: Taketoshi Fujimori, Ichikai; Yukihiro Ohashi; Akira Kawamata, both of Utsunomiya, all of Japan

[73] Assignee: Kao Corporation, Tokyo, Japan

[21] Appl. No.: 144,411

[22] Filed: Nov. 2, 1993

[30] Foreign Application Priority Data

Nov. 2, 1992 [JP] Japan .................. 4-294504

[51] Int. Cl.6 .................. A61K 31/70; A61K 31/16
[52] U.S. Cl. .................. 514/25; 514/625; 514/627; 514/629; 514/649; 514/671; 514/678; 514/847; 564/463; 564/502; 564/503; 564/504
[58] Field of Search ................. 514/25, 625, 627, 629, 514/649, 671, 678, 847; 564/463, 502, 503, 504

[56] References Cited

FOREIGN PATENT DOCUMENTS

| | | |
|---|---|---|
| 0227994 | 7/1987 | European Pat. Off. . |
| 0282816 | 9/1988 | European Pat. Off. . |
| 0398272 | 11/1990 | European Pat. Off. . |
| 0474023 | 3/1992 | European Pat. Off. . |
| 2404070 | 8/1975 | Germany . |
| 2421618 | 11/1975 | Germany . |
| 54-147937 | 11/1979 | Japan . |
| 63-216852 | 9/1988 | Japan . |
| 64-31752 | 2/1989 | Japan . |
| 3115223 | 5/1991 | Japan . |
| 93/05763 | 4/1993 | WIPO . |

OTHER PUBLICATIONS

Imokawa, G. et al., *J. Soc. Cosmet. Chem.* 1989, 40, 273–285.

*Primary Examiner*—Douglas W. Robinson
*Assistant Examiner*—Kathleen Kahler Fonda
*Attorney, Agent, or Firm*—Oblon, Spivak, McClelland, Maier & Neustadt

[57] ABSTRACT

Amino derivatives represented by the following general formula (1):

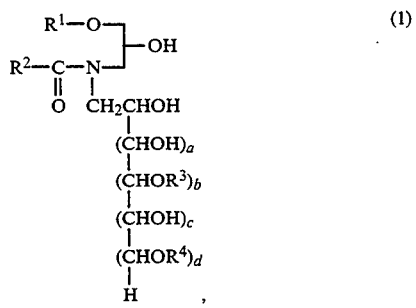

and external skin care preparations containing such an amide derivative, are useful for preventing or curing skin roughness. Intermediates useful for the preparation of such amides are also disclosed.

17 Claims, No Drawings

AMIDE DERIVATIVE AND EXTERNAL SKIN CARE PREPARATION CONTAINING THE SAME

BACKGROUND OF THE INVENTION

Field of the Invention

The present invention relates to amide derivatives which can enhance the water-retaining ability of the horny layer of skin and have an excellent effect of improving skin roughness, intermediates for the production of such amide derivatives, external skin care preparations containing such an amide derivative, and methods of moisturizing skin by applying such skin care preparations to skin.

Discussion of the Background

The water content of the horny layer of skin is known to be critical for imparting moisture to the skin to maintain skin smoothness and softness. The retention of water in the horny layer is said to depend upon the presence of a water-soluble component in the horny layer, namely, a free amino acid, organic acid, urea or inorganic ions. In the above circumstances, these materials have been incorporated either singly or in combination in medicinal external skin care preparations or cosmetic compositions with a view toward improving or preventing skin roughness. In addition, many humectants having high affinity with water have also been developed and have been used for improving the skin roughness.

However, these humectants remain on the skin surface when they are applied to the skin, so that they serve to supply water to the horny layer. Moreover, the effects of such compounds are temporary, and they do not basically improve the water-retaining ability of the horny layer itself or prevent or cure skin roughness substantially.

Thus, there remains a need for compounds which can enhance the water-retaining ability of the horny layer of skin and can improve skin roughness. There also remains a need for intermediates useful for the synthesis of such compounds. In addition, there remains a need for skin preparations and methods for treating rough skin.

SUMMARY OF THE INVENTION

Accordingly, it is an object of the present invention to provide novel compounds capable of basically improving the water-retaining ability of the horny layer of skin to prevent or cure skin roughness.

It is another object of the present invention to provide intermediates useful for the preparation of such compounds.

It is another object of the present invention to provide skin care preparations containing such compounds.

It is another object of the present invention to provide methods for moisturizing skin.

These and other objects, which will become apparent during the following detailed description, have been achieved by the inventors' discovery that an amide derivative represented by the following general formula (1) can basically prevent or cure skin roughness. Moreover, an intermediate from which the amide derivative can be prepared advantageously has also been found.

In a first aspect of the present invention, there is thus provided an amide derivative represented by the following general formula (1):

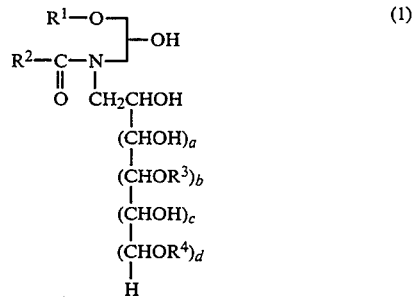

wherein $R^1$ is a linear or branched, saturated or unsaturated hydrocarbon group having 10–26 carbon atoms, $R^2$ is a hydrogen atom or a linear or branched, saturated or unsaturated hydrocarbon group having 1–31 carbon atoms, $R^3$ and $R^4$ are individually a hydrocarbon group which has 1–12 carbon atoms and may contain an oxygen atom, and a, b, c, and d are individually a number of 0–3, with the proviso that b and d are not 0 at the same time.

In another aspect of the present invention, there is also provided an external skin care preparation comprising an amide derivative represented by the formula (1).

In a further aspect of the present invention, there is provided an amine derivative which is useful as an intermediate for preparation of the amide derivative (1) and is represented by the following general formula (2):

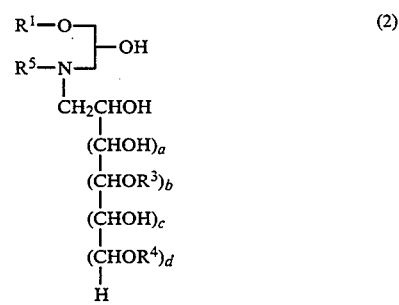

wherein $R^5$ is a hydrogen atom or a benzyl group, and $R^1$, $R^3$, $R^4$, a, b, c and d have the same meanings as defined above.

In yet a further aspect of the present invention, there is provided a method for moisturizing skin by applying a skin care preparation containing the amide derivative of formula (1) to skin.

The external skin care preparations according to the present invention exhibit excellent effects in enhancing the water-retaining ability of the horny layer and improving skin roughness. The use of the intermediate (2) according to the present invention makes it possible to advantageously prepare the amide derivative (1).

DETAILED DESCRIPTION OF THE PREFERRED EMBODIMENTS

In the general formulae (1) and (2), the linear or branched, saturated or unsaturated hydrocarbon group expressed by $R^1$ and having 10–26 carbon atoms may preferably be a linear or branched alkyl or alkenyl group having 10–26 carbon atoms, with a linear or branched alkyl group having 10–26 carbon atoms being particularly preferred. Specific examples of $R^1$ include decyl, dodecyl, tetradecyl, hexadecyl, octadecyl, eicosyl and tetraeicosyl groups, and the like. The linear or branched, saturated or unsaturated hydrocarbon group expressed by $R^2$ and having 1–31 carbon atoms may preferably be a linear or branched alkyl or alkenyl group having 1–31 carbon atoms, with a linear or branched alkyl group having 10–26 carbon atoms being particularly preferred. Specific examples of $R^2$ include methyl, ethyl, propyl, pentyl, heptyl, nonyl, monodecyl, tridecyl, pentadecyl, heptadecyl, nonadecyl and eicosyl groups, and the like.

Examples of the hydrocarbon groups, which are expressed by $R^3$ and $R^4$ have 1–12 carbon atoms and may contain an oxygen atom, include linear or branched alkyl groups having 1–12 carbon atoms, 2,3-dihydroxypropyl group, 2-hydroxyethyl group, 2-bis(2-hydroxyethyl)-3-hydroxypropyl group, 2,3,4,5,6-pentahydroxyhexyl group, sugar residues (e.g., glucopyranosyl, galactopyranosyl, gulopyranosyl, fructofuranosyl, etc.) and the like. It should be understood that the phrase "may contain an oxygen atom" as used in the context of the definition of $R^3$ and $R^4$ means that the group may contain one or more oxygen atoms in the form of: (a) one or more hydroxyl substituents on the hydrocarbon group; (b) one or more carbonyl groups in the hydrocarbon group; and one or more $C_{1-4}$ alkoxy substituents on the hydrocarbon group. It should also be understood that when one of $R^3$ and $R^4$ is a sugar residue, the molecule may exist as an equilibrium mixture of open and various cyclic forms of the sugar. Thus, in the cyclic form, the $R^3$ and/or $R^4$ group will contain oxygen atoms in the form of hydroxyl groups and as the ether linkage in the acetal group of the cyclic sugar.

Suitably, the sum of $a+b+c+d$ is 1 to 12. Preferably, $a+b+c+d$ is 1 to 4. Suitably, a is 0–3, b is 0 or 1, c is 0–2.

The amide derivative according to the present invention can be prepared, for example, in accordance with the following reaction scheme.

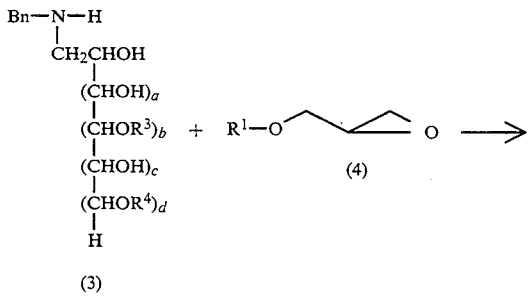

(3)

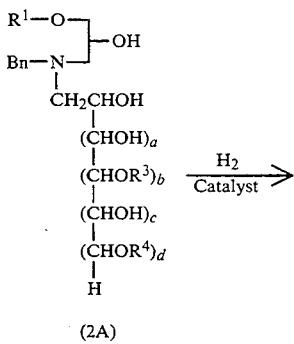

(2A)

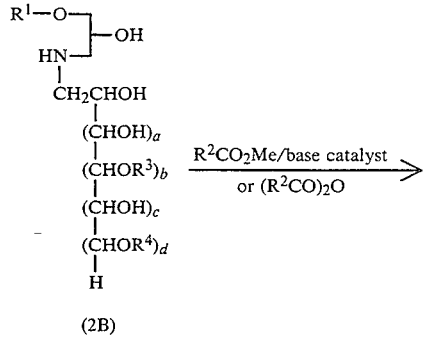

(2B)

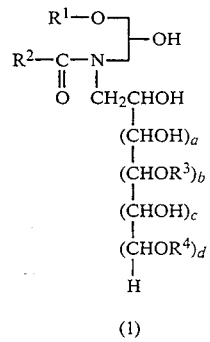

(1)

wherein Bn means a benzyl group, and $R^1$, $R^2$, $R^3$, $R^4$, a, b, c and d have the same meanings as defined above.

More specifically, the amide derivative according to the present invention can be prepared by reacting a benzylamine derivative (3) with a glycidyl ether (4), subjecting the resulting benzylamine derivative (2A) to hydrogenolysis to debenzylate it into an amine derivative (2B) and then acylating only the secondary amino group of the compound (2B).

The reaction between the benzylamine derivative (3) and the glycidyl ether (4) is carried out by stirring them at 25°–150° C. for several tens of minutes to 24 hours either without any solvent or in a solvent of a lower alcohol such as methanol, ethanol, propanol or isopropanol. Examples of the benzylamine derivative (3) used as the starting material include N-benzyl-3-(2-hydroxyethoxy)-2-hydroxypropylamine, N-benzyl-3-[2-bis(2-hydroxyethyl)-3-hydroxypropoxy]-2-hydroxypropylamine, N-benzyl-3-(2,3-dihydroxypropoxy)-2-hydroxypropylamine, N-benzyl-3-[2,3-(dimethylmethylenedioxy)propoxy]-2-hydroxypropylamine, N-benzyl-3-D-glucopyranosyloxy-2-hydroxypropylamine, N-benzyl-3-D-galactopyranosyloxy-2-hydroxypropylamine, N-benzyl-3-(2,3,4,5,6-pentahydroxyhexyloxy)-2-hydroxypropylamine, N-benzyl-4-α-D-glucopyranosyloxy-2,3,5,6-tetrahydroxyhexylamine, N-benzyl-4-β-D-glucopyranosyloxy-2,3,5,6-tetrahydroxyhexylamine, N-benzyl-4-α-D-galactopyranosyloxy-2,3,5,6-tetrahydroxyhexylamine, N-benzyl-6-α-D-glucopyranosyloxy-2,3,4,5-tetrahydroxyhexyl-amine, N-benzyl-6-α-D-galactopyranosyloxy-2,3,4,5-tetrahydroxyhexylamine and the like. If a compound having a protective group for the hydroxyl group such as N-benzyl-3-[2,3-(dimethylmethylenedioxy)propoxy]-2-hydroxypropylamine is used, it is only necessary to eliminate the protective group by an acid treatment after the reaction.

The compounds of formula (3) may be prepared by reacting benzylamine, $BnNH_2$, with an appropriate glycidyl ether of the formula (5)

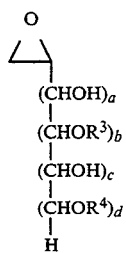

(5)

under the same types of conditions described above for the reaction of the glycidyl ether (4) with benzylamine derivative (3).

Alternatively, benzylamine derivative (8) (benzyl amine derivative (2A) in which a=c=d=0, b=1) may be prepared according to the following reaction scheme,

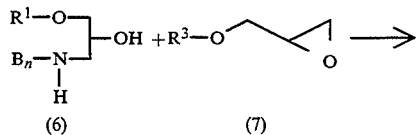

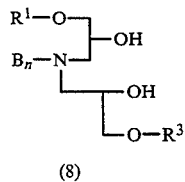

wherein, Bn represents a benzyl group, $R^1$ and $R^3$ have the same meanings as defined above.

Meanwhile, it is known that the following amine derivative (9) can be prepared by reacting a sugar such as glucose with benzylamine under a reductive condition according to the following reaction scheme (Carbohydrate Research, 82, 135–140 (1980)).

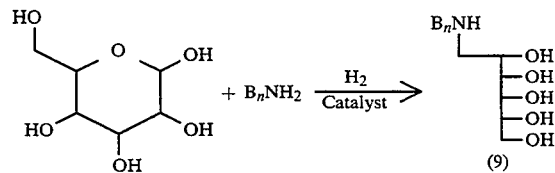

By utilizing this reaction, the following amine derivative (11) (amine derivative (2B) in which a=b=1, c=2, d=0) can be prepared by reacting the following amine derivative (10) with a sugar such as maltose and a sugar derivative under a reductive condition in accordance with the following reaction scheme,

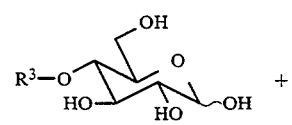

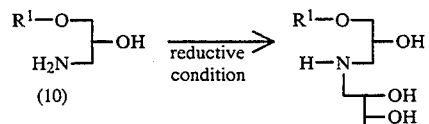

wherein $R^1$ and $R^3$ has the same meaning as defined above.

The resultant compound (2A) is debenzylated into the compound (2B). The debenzylation of the compound (2A) is carried out by subjecting the compound (2A) to hydrogenolysis in the presence of a catalyst such as palladium on active carbon or palladium black under normal pressure to 150 atm for several hours to several days in a solvent such as dioxane, tetrahydrofuran, methanol, ethanol or acetic acid.

Alternatively, compound 2A may be prepared by first reacting benzylamine, $BnNH_2$ with glycidyl ether (4) to obtain compound (6)

under the same types of conditions described above for the reaction of glycidyl ether (4) with benzylamine derivative (3). Compound (6) may then be reacted with glycidyl ether (5) under the same types of conditions to afford compound (2A).

The thus-obtained compounds (2A) and (2B) are novel compounds and important intermediates for efficiently obtaining the intended amide derivative (1). In addition, the following reaction can be considered for directly obtaining a compound such as the amine derivative (2B) from a glycidyl ether and a primary amine derivative.

wherein $R^6$ is a hydrocarbon group, and X is an oxygen-containing hydrocarbon group.

In this case, however, it is necessary to use the primary amine in excess. There is also a drawback that since such primary amines often have a high boiling point, it is difficult to remove it after the reaction.

The resulting compound (2B) can be acylated into the intended amide compound (1). The acylation of the amino group of the compound (2B) is achieved, for example, by reacting a lower alkyl ester of a fatty acid with the compound (2B) in the presence of a base catalyst such as sodium hydroxide, potassium hydroxide, sodium methoxide or potassium t-butoxide while distilling out a lower alcohol formed, or reacting a fatty acid anhydride such as palmitic anhydride, stearic anhydride or isostearic anhydride with the compound (2B) in a solvent such as tetrahydrofuran, dioxane or chloroform.

The amide derivative (1) thus prepared has an effect of enhancing the water-retaining ability of the horny layer of the skin and can hence be incorporated as a moisturizer in an external skin care preparation.

The external skin care preparations according to the present invention comprise one or more base ingredients for the conventional external skin care preparations and the amide derivative represented by the general formula (1) incorporated therein, and may be classified roughly into emulsion-type external skin care preparations and oil-based external skin care preparations from a viewpoint of form.

No particular limitation is imposed on the proportion of the amide derivative (1) in the external skin care preparations according to the present invention. In the case of the emulsion-type external skin care preparation, however, it is preferable to incorporate 0.001–50 wt. %, based on the total weight of the composition, of the amide derivative (1) in the conventionally-used base ingredients (for example, an oily substance, emulsifier, and water). In the case of the oil-based external skin care preparation on the other hand, it is preferable to incorporate 0.01–50 wt. % based on the total weight of the composition, of the amide derivative (1) in an oily base (for example, a liquid hydrocarbon such as squalane).

The external skin care preparations according to the present invention may be classified roughly into medicinal external skin care preparations and cosmetic compositions from the viewpoint of application.

Examples of the medicinal external skin care preparations include various ointments containing one or more medicinally-effective ingredients. Ointments include both those containing an oily base as a base and those containing an oil/water or water/oil emulsion-type base as a base. No particular limitation is imposed on oily bases. Plant oils, animal oils, synthetic oils, fatty acids, natural and synthetic glycerides, etc. may be mentioned. No particular limitation is imposed on medicinally-effective ingredients. For example, one or more of analgesic and antiphlogistic agents, antipruritics, disinfectants, astringents, emollients, hormones and the like may be used suitably as needed.

Where used as a cosmetic composition, it is possible to mix, in addition to the amide derivative according to the present invention as an essential ingredient, those ingredients employed routinely as cosmetic ingredients such as oily substances, moisturizers, ultraviolet absorbents, alcohols, chelating agents, pH adjustors, antiseptics, thickeners, coloring matter, perfume bases and the like in combination as needed.

As cosmetics, skin cosmetic compositions of various forms may be formulated including, for example, oil/water or water/oil type emulsified cosmetics, creams, cosmetic emulsions, toilet waters, oily cosmetics, lip sticks, foundations, skin cleansing compositions, hair tonics, hair styling compositions, hair grooming compositions, hair growth stimulants, etc.

In another embodiment, the present invention provides a method for moisturizing skin by applying to the skin an effective amount of the amide of formula (1). Typically, the amide will be applied in the form of one of the compositions described above. In preferred embodiments, the amide is applied to those areas of skin which are susceptible to becoming rough or have already become rough, such as the face, the hands, the feet, the arms, the elbows, the legs, and the knees. Suitably, the amide is applied in an amount of $3.0 \times 10^{-8}$ to $1.5 \times 10^{-3}$ g/cm$^2$ of skin, preferably $3.0 \times 10^{-5}$ to $6.0 \times 10^{-4}$ g/cm$^2$ of skin. Typically, the amide is applied to the skin 1 to 3 times per day until the skin roughness abates. Alternatively, the amide may be applied daily for an indefinite period of time to help prevent the onset of rough skin.

Other features of the invention will become apparent in the course of the following descriptions of exemplary embodiments which are given for illustration of the invention and are not intended to be limiting thereof.

EXAMPLES

Example 1

Synthesis of N-(3-hexadecyloxy-2-hydroxypropyl)-N-[3-(2,3-dihydroxypropoxy)-2-hydroxypropyl]hexadecanamide (1a):

(1) Synthesis of N-benzyl-3-[2,3-(dimethylmethylenedioxy)propoxy]-2-hydroxypropylamine (3a) [in the general formula (3), R$^4$ (2 3-dimethylmethylenedioxy)propyl, a=b =c=0, d=1]:

A 500-ml three-necked flask equipped with a dropping funnel, thermometer and reflux condenser was charged with 174 ml (1.59 mol) of benzylamine and 48.0 ml of ethanol. While heating and stirring the mixture at 80° C. in a nitrogen atmosphere, 20.3 g (0.11 mol) of 2,3-(dimethylmethylenedioxy)propyl glycidyl ether were added dropwise over 2 hours. After completion of the addition, the heating and stirring were continued for an additional 1 hour under the same conditions. After the reaction mixture was concentrated under reduced pressure, the resulting residue was purified by flash chromatography on silica gel, thereby obtaining 20.4 g (yield: 64%) of the title compound (3a) as a pale yellow oil.

IR (NaCl, cm$^{-1}$): 3324, 2932, 2900, 2876, 1374, 1258, 1214, 1140, 1128, 1118, 1104, 1082, 1054, 842, 700.

$^1$H-NMR (CDCl$_3$, δ): 1.36(s,3H), 1.43(s, 3H), 2.57–2.76(m, 3H), 3.41–4.06(m,10H), 4.20–4.31(m, 1H), 7.18–7.40 (m, 5H).

(2) Synthesis of N-3-(3-hexadecyloxy-2-hydroxypropyl)-N-[3-(2,3-(dihydroxypropoxy)-2-hydroxypropyl]benzylamine (2Aa) [in the general formula (2A), R$^1$=C$_{16}$H$_{33}$, R$^4$=CH$_2$CH(OH)CH$_2$OH, a=b=c=0, d=1]:

A 500-ml three-necked flask equipped with a dropping funnel, thermometer and reflux condenser was charged with 22.1 g (74.9 mmol) of the compound (3a) obtained in the above step (1) and 6.62 g of ethanol. While heating and stirring the mixture at 80° C. under a nitrogen atmosphere, 33.6 g (0.11 mol) of hexadecyl glycidyl ether were added dropwise over 4 hours. After completion of the addition, the heating and stirring were continued for an additional 30 minutes under the same conditions. After the reaction mixture was concentrated under reduced pressure, the resulting residue was transferred to a 200-ml eggplant type flask equipped with a reflux condenser and added with 15.4 g of isopropyl alcohol, 38.4 g of water and 5.14 g of sulfuric acid. While stirring the mixture, it was heated under reflux for 2 hours under a nitrogen atmosphere. Thereafter, the reaction mixture was neutralized with aqueous sodium hydroxide, and then concentrated under reduced pressure. Ethanol was added to the resulting residue to separate insoluble matter by filtration. The filtrate was concentrated again under reduced pressure. The residue thus obtained was purified by flash chromatography on silica gel, thereby obtaining 34.8 g (yield: 84%) of the title compound (2Aa) as a pale yellow oil.

IR (NaCl, cm$^{-1}$): 3380, 2928, 2856, 1466, 1458, 1128, 1118, 1076, 1054, 1046, 700.

$^1$H-NMR (CDCl$_3$, δ): 0.88(t,J=6.40 Hz,3H), 1.16–1.60(m,28H), 2.53–2.69(m,4H), 3.32–4.23(m,19H), 7.20–7.40(m,5H).

(3) Synthesis of N-(3-hexadecyloxy-2-hydroxypropyl)-3-(2,3-dihydroxypropoxy)-2-hydroxypropylamine (2Ba) [in the general formula (2B), R$^1$=C$_{16}$H$_{33}$, R$^4$=CH$_2$CH(OH)CH$_2$OH, a=b=c=0, d=1]:

A 300-ml autoclave was charged with 21.4 g (38.6 mmol) of the compound (2Aa) obtained in the above step (2), 1.07 g of palladium black and 200-ml of methanol to subject the compound (2Aa) to hydrogenolysis at 50° C. for 36 hours under a hydrogen pressure of 100 kg/cm$^2$. After the catalyst was separated by filtration, the residue was allowed to cool, thereby obtaining 11.1 g (yield: 62%) of the title compound (2Ba) as a colorless solid in the form of crystals.

Melting point: 111.8°–113.0° C.

IR (KBr, cm$^{-1}$): 3440, 2924, 2856, 1470, 1124.

$^1$H-NMR (CDCl$_3$, δ):0.86(t,J=6.40 Hz,3H), 1.20–1.41(m,28H), 2.48–2.57 (m, 4H), 3.23–3.60 (m, 15H), 3.67–3.90(m,3H).

(4) Synthesis of N-(3-hexadecyloxy-2-hydroxypropyl)-N-[3-(2,3-dihydroxypropoxy)-2-hydroxypropyl]hexadecanamide (1a) [in the general formula (1), R$^1$=C$_{16}$H$_{33}$, R$^2$=C$_{15}$H$_{31}$, R$^4$ =CH$_2$CH(OH)CH$_2$OH, a=b=c=0, d=1]:

A 300-ml three-necked flask equipped with a dropping funnel, thermometer and Dean-Stark trap was charged with 15.0 g (32.3 mmol) of the compound (2Ba) obtained in the above step (3), 150 ml of benzene and 0.31 g of a 28% solution of sodium methoxide in methanol, and the mixture was heated and stirred at 80° C. While distilling out methanol, a solution of 9.17 g (33.9 mmol) of methyl palmitate in 25 ml of benzene was added dropwise over 1.5 hours. After completion of the addition, the heating and stirring were continued for an additional 2 hours under the same conditions. After the reaction mixture was concentrated under reduced pressure, the resulting residue was purified by flash chromatography on silica gel, thereby obtaining 18.0 g (yield: 78%) of the title compound (1a) as a colorless solid.

Melting point: 78.2°–79.0° C.

IR (KBr, cm$^{-1}$): 3420, 2924, 2852, 1624, 1468, 1114.

$^1$H-NMR (CDCl$_3$, δ): 0.85–0.95 (m,6H), 1.25–1.70 (m,54H), 2.35–2.50(m,2H), 3.20–3.70(m,18H), 3.80–4.20(m,3H).

EXAMPLE 2

Synthesis of N-(3-hexadecyloxy-2-hydroxypropyl)-N-(3-D-glucopyranosyloxy-2-hydroxypropyl)hexadecanamide (1b):

(1) Synthesis of N-(3-hexadecyloxy-2-hydroxypropyl)-N-(3-D-glucopyranosyloxy-2-hydroxypropyl)-benzylamine (2Ab) [in the general formula (2A), R$^1$=C$_{16}$H$_{33}$,

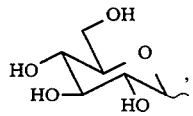

A 300-ml three-necked flask equipped with a dropping funnel and reflux condenser was charged with 34.9 g (88.7 mmol) of N-(3-hexadecyloxy-2-hydroxypropyl)-benzylamine and 7.11 g of ethanol. While heating and stirring the mixture at 80° C. under a nitrogen atmosphere, 45 ml of a solution of 15.4 g (65.2 mmol) of 2,3-epoxypropyl D-glucopyranoside in ethanol were added dropwise over 3 hours. After completion of the addition, the heating and stirring were continued for an additional 3 hours under the same conditions. After the reaction mixture was concentrated under reduced pressure, the resulting residue was purified by flash chromatography on silica gel, thereby obtaining 35.6 g (yield: 80%) of the title compound (2Ab) as a pale yellow oil.

IR (NaCl, cm$^{-1}$): 3400, 2920, 2860, 1458, 1368, 1296, 1260, 1106, 1074, 740, 698.

$^1$H-NMR (CDCl$_3$, δ): 0.89(t,J=6.42 Hz,3H), 1.15–1.67(m,28H), 2.37–2.74(m,4H), 3.20–4.94(m,23H), 7.20–7.60 (m, 5H).

(2) Synthesis of N-(3-hexadecyloxy-2-hydroxypropyl)-3-D-glucopyranosyloxy-2-hydroxypropylamine (2Bb) [in the general formula (2B), R$^1$=C$_{16}$H$_{33}$,

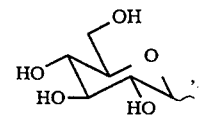

A 300-ml autoclave was charged with 24.6 g (40.9 mmol) of the compound (2Ab) obtained in the above step (1), 249 mg of palladium black and 240 ml of methanol. The resulting mixture was stirred at 50° C. for 72 hours under a hydrogen pressure of 100 kg/cm$^2$. The catalyst was removed by filtering the hot mixture, and the filtrate was concentrated under reduced pressure. The resulting residue was recrystallized from methanol, thereby obtaining 14.7 g (yield: 65%) of the title compound (2Bb) as a colorless solid.

IR (KBr, cm$^{-1}$): 3368, 2920, 2852, 1470, 1120, 1070, 1032.

$^1$H-NMR (CDCl$_3$, δ): 0.85–1.70(m,3H), 2.40–5.00 (m,26H).

(3) Synthesis of N-(3-hexadecyloxy-2-hydroxypropyl) -N-(3-D-glucopyranosyloxy-2-hydroxypropyl)hexadecanamide (1b) [in the general formula (1) R$^1$=C$_{16}$H$_{33}$, R$^2$=C$_{15}$H$_{31}$, R$^4$—

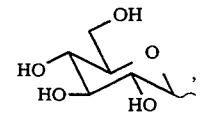

, a=b=c=0, d=1]:

A 500-ml three-necked flask equipped with a dropping funnel and Dean-Stark trap was charged with 16.1 g (29.2 mmol) of the compound (2Bb) obtained in the above step (2), 240 ml of benzene and 1.60 g of a 28% solution of sodium methoxide in methanol, and the mixture was heated and stirred at 80° C. While distilling out methanol, 15 ml of a solution of 8.70 g (32.2 mmol) of methyl palmitate in benzene was added dropwise over 1 hour. After completion of the addition, the stirring was continued for an additional 4.5 hours under the same conditions, and the reaction mixture was concentrated under reduced pressure. The resulting residue was purified by flash chromatography on silica gel, thereby obtaining 12.0 g (yield: 52%) of the title compound (1b) as a colorless solid.

IR (KBr, cm$^{-1}$): 3428, 2924, 2856, 1624, 1470, 1112, 1076, 1038.

1H-NMR (CDCl$_3$, δ): 0.88(t,J=6.40 Hz,6H), 1.26–1.69 (m,54H), 2.26–2.47 (m,2H), 2.93–5.57 (m,25H).

EXAMPLE 3

Synthesis of 1-[N-(3-hexadecyloxy-2-hydroxypropyl)hexadecanoylamino]-1-deoxy-3-O-α-D-glucopyranosyl-D-glucitol (1c):

(1) Synthesis of 1-[N-(3-hexadecyloxy-2-hydroxypropyl)-benzylamino]-1-deoxy-3-O-α-D-glucopyranosyl-D-glucitol (2Bc) [in the general formula (2B), $R^1 = C_{16}H_{33}$, $R_3 =$

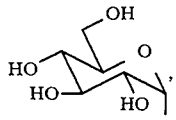

, a=b=1, c=2, d=0]:

A 1-liter eggplant type flask equipped with a reflux condenser was charged with 22.7 g (72 mmol) of 1-amino-3-hexadecyloxy-2-propanol, 23.5 g (69 mmol) of maltose and 350 g of methanol. After stirring the mixture for 20 hours at room temperature under a nitrogen atmosphere, it was heated and stirred at 80° C. for 1 hour. The thus-obtained solution was transferred to a 970-ml autoclave, and 2.26 g of palladium on carbon was added, thereby subjecting the solution to hydrogenolysis at 50° C. for 16 hours under a hydrogen pressure of 100 kg/cm$^2$. The catalyst was removed by filtering the hot mixture, and the filtrate was allowed to cool to form crystals. The crystals were recrystallized again from methanol, thereby obtaining 15.2 g (yield: 33%) of the title compound (2Be) as a colorless solid.

IR (KBr, cm$^{-1}$): 3396(br), 2920, 2852, 1466, 1028.

1H-NMR (CDCl$_3$-D$_2$O, δ): 0.88(t,J=6.48Hz,3H), 1.12–2.10(m,28H), 2.40–2.85 (m, 4H), 3.25–4.30 (m, 17H), 5.07 (br, 1H).

(2) Synthesis of 1-[N-(3-hexadecyloxy-2-hydroxypropyl)hexadecanoylamino]-1-deoxy-3-O-α-D-glucopyranosyl-D-glucitol (1c) [in the general formula (2), $R^1 = C_{16}H_{33}$, $R^2 = C_{15}H_{31}$, $R^3 =$

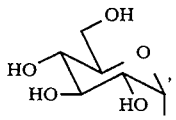

, a=b=1, c=2, d=0]:

A 500-ml eggplant type flask was charged with 5.00 g (77 mmol) of the compound (2Bc) obtained in the above step (1), 4.12 g (83 mmol) of palmitic anhydride and 100 ml of chloroform. The resulting mixture was heated and stirred at 80° C. for 30 minutes in a nitrogen atmosphere. After the mixture was concentrated under reduced pressure, it was recrystallized from methanol, thereby obtaining 1.52 g (yield: 22%) of the title compound (1c) as a colorless solid.

IR (KBr, cm$^{-1}$): 3400 (br), 2920, 1618, 1466, 1078, 1034.

1H-NMR (CDCl$_3$-D$_2$O, δ): 0.88(t,J=6.04 Hz,6H), 1.12–1.75 (m,54H), 2.30–2.55 (m, 2H), 3.15–4.18 (m, 21H), 5.02 (d,J=3.86Hz, 1H).

EXAMPLE 4

Mixtures, each of which had been formulated by mixing one of the amide derivatives (1a) to (1c) shown in Table 2 and vaseline at a weight ratio of 1:3, were evaluated in skin conductance and skin roughness by the following methods. The results are shown in Table 3.

(Testing methods)

Chosen as volunteers in winter were ten women of 20–50 years of age who had skin roughness on their both cheeks. Different external skin care preparations were coated separately on the left and right cheeks of each volunteer for 2 weeks. On the following day of the completion of the two-week coating test, tests were conducted with respect to the following properties.

(1) Skin conductance:

After washing the face with warm water of 37° C., each volunteer was allowed to rest for 20 minutes in a room which was air-conditioned at 20° C. and 40% humidity. The water content of her horny layer was measured by a skin conductance meter (manufactured by IBS Company). A smaller conductance value indicates greater skin roughness. Conductance values of 5 and smaller indicate severe skin roughness. On the contrary, no substantial skin roughness is observed where this value is 20 or greater.

(2) Score of skin roughness:

Skin roughness was observed visually and ranked in accordance with the following standard shown in Table 1. Each score indicates an average value.

TABLE 1

| Score | Ranking of skin roughness |
|---|---|
| 0 | No skin roughness was observed. |
| 1 | Slight skin roughness was observed. |
| 2 | Skin roughness was observed. |
| 3 | Rather severe skin roughness was observed. |
| 4 | Severe skin roughness was observed. |

TABLE 2

| | Amide derivative | | |
|---|---|---|---|
| | 1a | 1b | 1c |
| R1 | $C_{16}H_{33}$ | $C_{16}H_{33}$ | $C_{16}H_{33}$ |
| R2 | $C_{15}H_{31}$ | $C_{15}H_{31}$ | $C_{15}H_{31}$ |
| R3 | | | ![glucopyranosyl] |
| R4 | CH$_2$—<br>\|<br>CHOH<br>\|<br>CH$_2$OH | ![glucopyranosyl] | ![glucopyranosyl] |
| a | 0 | 0 | 1 |
| b | 0 | 0 | 1 |
| c | 0 | 0 | 2 |
| d | 1 | 1 | 0 |

TABLE 3

| | Amide Derivative | Skin Conductance | Score of Skin Roughness |
|---|---|---|---|
| Invention product | 1a | 15 | 1.5 |
| Invention product | 1b | 16 | 1.4 |
| Invention product | 1c | 18 | 1.2 |
| Comparative* product | — | 6 | 2.4 |

*The comparative product used contained only vaseline.

As apparent from Table 3, the amide derivatives (1) according to the present invention each have an excellent effect of enhancing the water-retaining ability of the horny layer and exhibited a superb effect of improving skin roughness.

EXAMPLE 5

Using separately the amide derivatives 1a–1c used in Example 4, external skin care preparations (emulsified cosmetic compositions) corresponding to the compositions shown in Table 4 were formulated to evaluate them in regard to their effect for the improvement of skin roughness in the same manner as in Example 4. The results are shown in Table 5.

TABLE 4

|  | Invention Product | Comparative Product |
| --- | --- | --- |
| Methyl-branched isostearyl glyceryl ether | 2.0 | 2.0 |
| 2-Octyldodecyl myristate | 10.0 | 10.0 |
| Vaseline | 3.0 | 3.0 |
| Squalane | 5.0 | 5.0 |
| Tocopherol acetate | 0.5 | 0.5 |
| Amide derivative (1a, 1b or 1c) | 1.0 | — |
| Water | Balance | Balance |

TABLE 5

|  | Amide Derivative | Score of Skin Roughness |
| --- | --- | --- |
| Invention product | 1a | 1.3 |
| Invention product | 1b | 1.1 |
| Invention product | 1c | 1.0 |
| Comparative product | — | 2.3 |

As apparent from Table 5, the external skin care preparations according to the present invention each have an excellent effect of improving skin roughness.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. An amide represented by the following formula (1):

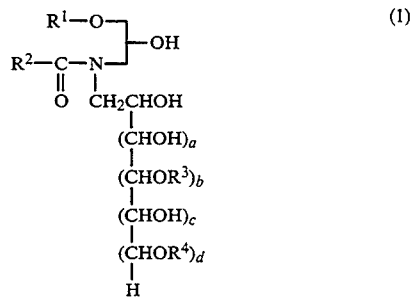

wherein $R^1$ is a linear or branched, saturated or unsaturated hydrocarbon group having 10–26 carbon atoms, $R^2$ is a linear or branched alkyl group having 10–26 carbon atoms, $R^3$ and $R^4$ are individually a hydrocarbon group which has 1–12 carbon atoms and may contain an oxygen atom, and a, b, c and d are individually a number of 0–3, with the proviso that b and d are not 0 at the same time.

2. The amide according to claim 1, wherein $R^1$ is a linear or branched alkyl or alkenyl group having 10–26 carbon atoms.

3. The amide according to claim 1, wherein $R^1$ is a linear or branched alkyl group having 10–26 carbon atoms.

4. The amide according to claim 1, wherein $R^3$ and $R^4$ are individually a group selected from the group consisting of alkyl groups having 1–12 carbon atoms, 2,3-dihydroxypropyl group, 2-hydroxyethyl group, 2-bis(2-hydroxyethyl)-3-hydroxypropyl group, 2,3,4,5,6-pentahydroxyhexyl group, glucopyranosyl, galactopyranosyl, gulopyranosyl, and fructofuranosyl.

5. The amide derivative according to claim 1, wherein $R^1$ is a linear or branched alkyl group having 10–26 carbon atoms, $R^2$ is a linear or branched alkyl group having 10–26 carbon atoms, and $R^3$ and $R^4$ are individually a group selected from the group consisting of alkyl groups having 1–12 carbon atoms, 2,3-dihydroxypropyl group, 2-hydroxyethyl group, 2-bis(2-hydroxyethyl)-3-hydroxypropyl group, 2,3,4,5,6-pentahydroxyhexyl group, glucopyranosyl, galactopyranosyl, gulopyranosyl, and fructofuranosyl.

6. An external skin care preparation comprising an amide represented by the following formula (1):

$$\begin{array}{c} R^1-O \\ R^2-C-N \\ \parallel \ \ | \\ O \ \ CH_2CHOH \\ | \\ (CHOH)_a \\ | \\ (CHOR^3)_b \\ | \\ (CHOH)_c \\ | \\ (CHOR^4)_d \\ | \\ H \end{array} \quad -OH \qquad (1)$$

wherein $R^1$ is a linear or branched, saturated or unsaturated hydrocarbon group having 10–26 carbons atoms, $R^2$ is a linear or branched alkyl group having 10–26 carbon atoms, $R^3$ and $R^4$ are individually a hydrocarbon group which has 1–12 carbon atoms and may contain an oxygen atom, and a, b, c, and d are individually a number of 0–3, with the proviso that b and d are not 0 at the same time, together with one or more skin care acceptable base ingredients.

7. The external skin care preparation according to claim 6, wherein said amide (1) is present in an amount of 0.001–50 wt. %, based on the total weight of said preparation.

8. The external skin care preparation according to claim 6, which comprises 0.001–50 wt. %, based on the total weight of said preparation, of said amide (1) and one or more skin care acceptable base ingredients, said preparation being in the form of an emulsion.

9. The external skin care preparation according to claim 6, which comprises 0.01–50 wt. %, based on the total weight of said preparation, of the amide derivative (1) and an oily base, said preparation being in the form of an oil-based preparation.

10. An amine represented by the following formula (2):

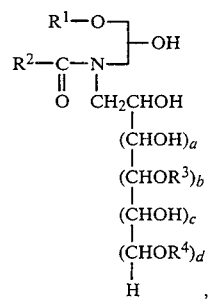

(1)

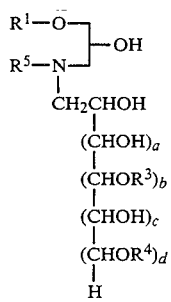

(2)

wherein $R^1$ is a linear or branched, saturated or unsaturated hydrocarbon group having 10-26 carbon atoms, $R^2$ is a linear or branched alkyl group having 10-26 carbon atoms, $R^3$ and $R^4$ are individually a hydrocarbon group which has 1-12 carbon atoms and may contain an oxygen atom, and a, b, c and d are individually a number of 0-3, with the proviso that b and d are not 0 at the same time.

14. The method of claim 13, wherein $R^1$ is a linear or branched alkyl or alkenyl group having 10-26 carbon atoms.

15. The method of claim 13, wherein $R^1$ is a linear or branched alkyl group having 10-26 carbon atoms.

16. The method of claim 13, wherein $R^3$ and $R^4$ are individually a group selected from the group consisting of alkyl groups having 1-12 carbon atoms, 2,3-dihydroxypropyl group, 2-hydroxyethyl group, 2-bis(2-hydroxyethyl)-3-hydroxypropyl group, 2,3,4,5,6-pentahydroxyhexyl group, glucopyranosyl, galactopyranosyl, gulopyranosyl, and fructofuranosyl.

17. The method of claim 13, wherein $R^1$ is a linear or branched alkyl group having 10-26 carbon atoms, $R^2$ is a linear or branched alkyl group having 10-26 carbon atoms, and $R^3$ and $R^4$ are individually a group selected from the group consisting of alkyl groups having 1-12 carbon atoms, 2,3-dihydroxypropyl group, 2-hydroxyethyl group, 2-bis(2-hydroxyethyl)-3-hydroxypropyl group, 2,3,4,5,6-pentahydroxyhexyl group, glucopyranosyl, galactopyranosyl, gulopyranosyl, and fructofuranosyl.

* * * * * wherein $R^1$ is a linear or branched, saturated or unsaturated hydrocarbon group having 10-26 carbon atoms, $R^3$ and $R^4$ are individually a hydrocarbon group which has 1-12 carbon atoms and may contain an oxygen atom, $R^5$ is a hydrogen atom or a benzyl group, and a, b, c, and d are individually a number of 0-3, with the proviso that b and d are not 0 at the same time.

11. The amine according to claim 10, wherein $R^1$ is a linear or branched alkyl or alkenyl group having 10-26 carbon atoms.

12. The amine according to claim 10, wherein $R^3$ and $R^4$ are individually a group selected from the group consisting of alkyl groups having 1-12 carbon atoms, 2,3-dihydroxypropyl group, 2-hydroxyethyl group, 2-bis(2-hydroxyethyl)-3-hydroxypropyl group, 2,3,4,5,6-pentahydroxyhexyl group, glucopyranosyl, galactopyranosyl, gulopyranosyl, and fructofuranosyl.

13. A method of moisturizing skin, comprising topically applying to the skin an effective amount of an amide of formula (1):